(12) United States Patent
Tanaka et al.

(10) Patent No.: US 6,410,753 B2
(45) Date of Patent: Jun. 25, 2002

(54) PROCESS FOR PRODUCING TRIMELLITIC ANHYDRIDE

(75) Inventors: Kazuo Tanaka; Hiroshi Ogawa; Ikutaro Maruki, all of Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/861,627

(22) Filed: May 22, 2001

(30) Foreign Application Priority Data

Jun. 9, 2000 (JP) ........................................ 2000-173925
Jun. 23, 2000 (JP) ........................................ 2000-189163

(51) Int. Cl.[7] ........................................... C07D 307/89
(52) U.S. Cl. ........................................ 549/245
(58) Field of Search ........................................ 549/245

(56) References Cited

U.S. PATENT DOCUMENTS 3,920,735 A    11/1975   Wampfler et al.
4,587,350 A  * 5/1986    Kilner et al. ................ 549/245

FOREIGN PATENT DOCUMENTS

JP        5-221919      8/1993
JP        2939346       6/1999

* cited by examiner

Primary Examiner—Charanjit S. Aulakh
(74) Attorney, Agent, or Firm—Armstrong, Westerman & Hattori, LLP

(57) ABSTRACT

A process for producing trimellitic anhydride which comprises performing liquid phase oxidation of pseudocumene containing 5% by weight or above of dimethyl bezaldehyde as a raw material for oxidation with air in aliphatic monocarboxylic acid having 1 to 5 carbon atoms as a solvent in the presence of a catalyst comprising both each metal of cobalt, manganese and zirconium and bromine to obtain trimellitic acid and then heat dehydrating trimellitic acid thus obtained or heat treating trimellitic acid thus obtained in the presence of a catalyst comprising 10 ppm or above of Ni thereby producing trimellitic anhydride.

17 Claims, No Drawings

PROCESS FOR PRODUCING TRIMELLITIC ANHYDRIDE

BACKGROUND OF THE INVENTION

1) Field on the Invention

The present invention relates to a process for producing trimellitic anhydride from trimellitic acid obtained by liquid phase oxidation of pseudocumene, in which obtained trimellitic anhydride is not colored and contents of by-products are very small.

2) Prior Art

Trimellitic anhydride which is an aromatic triacidic base is important as a raw material of high grade plasticizers or heat resisting plastics.

Trimellitic anhydride, for example, as described in Japanese Patent Kokai (Laid-open) No.61-280448, is produced by a process comprising heat dehydrating at a temperature of 220 to 230° C. crude trimellitic acid obtained by oxidation of pseudocumene with molecular oxygen in the presence of a catalyst comprising bromine ion or both bromine ion and a heavy metal(s) and then performing vacuum distillation.

Trimellitic anhydride produced by above-mentioned process does not always satisfy its quality. In recent years, further high quality of trimellitic anhydride has been required as a raw material of high grade plasticizers or heat resisting plastics.

Trimellitic acid is produced by oxidation of pseudocumene with air in the presence of a heavy metal catalyst in the same manner as in other alkyl aromatic compounds. Since two carboxyl groups in trimellitic acid thus produced have ortho-structure to each other, trimellitic acid forms a complex with a heavy metal(s) to degrade catalyst activity. Thus, it is known that the yield of trimellitic acid in use of psuedocumene is lower than that in use of alkyl aromatic compounds having no such structure.

Thus, various improvements in catalysts for oxidation of psuedocumene or other alkyl aromatic compounds have been performed. U.S. Pat. No. 3,920,735 describes that Mn—Br catalysts and Co—Mn—Br catalysts are improved by addition of zirconium. Japanese Patent No.2939346 describes a process for oxidation of psuedocumene comprising further using cerium in addition to a Co—Mn—Zr—Br catalyst and adding a Co—Mn—Zr—Ce—Br catalyst step by step. Japanease Patent Kokai (Laid-Open) No.5-221919 describes a process for oxidation of psuedocumene comprising a Co—Mn—Ce—Ti—Br catalyst step by step.

Trimellitic acid is usually dehydrated to change to trimellitic anhydride, which is used as an intermediate to synthesize resins or plasticizers. It is desired that trimellitic anhydride thus obtained and resins used it are not colored.

Japanese Publication (of PCT Application) No.4-501271 discloses a process for improving color of trimellitic anhydride comprising adding boron oxide of 0.1% by weight or above to trimellitic anhydride and performing heat treatment and then performing distillation.

The inventors oxidized psuedocumene according to the processes described in Japanese Patent No.2939346 and Japanese Patent Kokai (Laid-open) No.5-221919 and dehydrated trimellitic acid thus obtained to change trimellitic anhydride. Trimellitic anhydride thus obtained was colored to some degree.

In conventional processes for producing trimellitic anhydride, organic bromine compounds including, typically, bromotrimellitic acid are often by-produced since bromine ion is used as an oxidation catalyst. The organic bromine compounds are remained in distillation-purified trimellitic anhydride since they are difficult to separate, so that they exert bad influence on plasticizers or heat resisting plastics to use trimellitic anhydride as a raw material.

Thus, a process for producing trimellitic anhydride in which obtained trimellitic anhydride is not colored and contents of by-products such as organic bromine compounds are very small has been required.

SUMMARY OF THE INVENTION

An object of the present invention is to provide a process for producing trimellitic anhydride comprising performing liquid phase oxidation of psuedocumene to obtain trimellitic acid and producing trimellitic anhydride from trimellitic acid thus obtained, in which trimellitic anhydride is not colored and contents of by-products such as organic bromine compounds are very small.

As a result of extensive studies to solve above-mentioned prior art problems, the inventors have found that that trimellitic acid is produced by liquid phase oxidation of psuedocumene containing a specific amount of dimethyl benzaldehyde as raw material for oxidation and then intended trimellitic anhydride which is not colored can be produced from trimellitic acid thus obtained and furthermore trimellitic acid in which contents of by-products such as organic bromine compounds can be produced by heat treating trimellitic acid and/or trimellitic anhydride produced in above-mentioned process in the presence of a Ni catalyst for a long time and then purifying trimellitic anhydride thus obtained by distillation, and have accomplished the present invention.

The present invention provides to a process for producing trimellitic anhydride which comprises performing liquid phase oxidation of pseudocumene containing 5% by weight or above of dimethyl bezaldehyde as a raw material for oxidation with air in aliphatic monocarboxylic acid having 1 to 5 carbon atoms as a solvent in the presence of a catalyst comprising both each metal of cobalt, manganese and zirconium and bromine to obtain trimellitic acid and then heat dehydrating trimellitic acid thus obtained, thereby producing trimellitic anhydride.

The present invention provides to a process for producing trimellitic anhydride which comprises performing liquid phase oxidation of pseudocumene containing 5% by weight or above of dimethyl bezaldehyde as a raw material for oxidation with air in aliphatic monocarboxylic acid having 1 to 5 carbon atoms as a solvent in the presence of a catalyst comprising both each metal of cobalt, manganese and zirconium and bromine to obtain trimellitic acid and then heat treating trimellitic acid thus obtained in the presence of a catalyst comprising 10 ppm or above of Ni to trimellitic acid at a temperature of 200° C. or above for 30 minutes or above to produce trimellitic anhydride and then separating trimellitic anhydride thus produced by distillation.

Further, the present invention provides to a process for producing trimellitic anhydride which comprises performing liquid phase oxidation of pseudocumene, dimethyl benzaldehyde and/or oxide derivative of dimethyl benzaldehyde as raw material for oxidation with air in a solvent in the presence of a catalyst comprising a bromine compound to obtain trimellitic acid and then heat treating trimellitic acid thus obtained in the presence of a catalyst comprising 10 ppm or above of Ni to trimellitic acid and/or trimellitic anhydride at a temperature of 200° C. or above for 30 minutes or above to produce trimellitic anhydride and then separating trimellitic anhydride thus produced by distillation.

DETAILED DESCRIPTION OF THE INVENTION

The present invention will be described in detail below.

As psuedocumene to be used as a raw material for oxidation in the present invention, commercial psuedocumene separated by distillation from $C_9$ distillate in a catalytic reforming oil or a thermal decomposition residual oil can be used.

As dimethyl benzaldehyde to be used as a raw sub-material for oxidation, 3,4-dimethyl benzaldehyde, 2,4-dimethyl benzaldehyde, 2,5-dimethyl benzaldehyde and a mixture thereof can be used.

Dimethyl benzoic acids including 3,4-dimethyl benzoic acid, 2,4-dimethyl benzoic acid and 2,5-dimethyl benzoic acid may be contained in the raw material for oxidation.

In the present invention, psuedocumene containing dimethyl benzaldehyde of 5% by weight or above is used as the raw material for oxidation. It is preferable that the raw material for oxidation contains dimethyl benzaldehyde of 6% by weight or above. When the raw material contains dimethyl benzaldehyde, oxidation of psuedocumene is promoted and combustion and side reactions are decreased, so that the oxidation yield is improved. Thus, in subsequent dehydration, the product is not colored. Further, the content of 2,4-dimethyl benzaldehyde in psuedocumene is suitably decided in the above-mentioned range considering economy since 2,4-dimethyl benzaldehyde is more expensive than psuedocumene.

The solvent to be used in the liquid phase oxidation is aliphatic monocarboxylic acid having 1 to 5 carbon atoms. Formic acid, acetic acid, propionic acid, butyric acid and a mixture thereof are used, among which acetic acid and propionic acid are preferable and particularly, acetic acid is more preferable. It is preferable that a water content in the solvent is 10% by weight or below. The weight ratio of solvent to raw material for oxidation is 1/1 to 4/1 and preferably 1.5/1 to 3.0/1.

The catalyst for the liquid phase oxidation comprises each metal of cobalt, manganese and zirconium. The metals in the catalyst are used in the form of metal ion. The metals can be used as compounds such as organic acid salt and halogenide. Particularly, it is preferable that the metals are used as metal acetate or metal bromide.

The catalyst for the liquid phase oxidation further comprises bromine. The bromine in the catalyst is used in the form of bromine ion. As the bromine source to be used, any substance may be applied on the condition that it dissolves in the reaction system and generates bromine ion. Examples of the bromine source include inorganic bromides such as hydrogen bromide, sodium bromide and cobalt bromide and organic bromides such as tetrabromoethan. Among them, hydrogen bromide, cobalt bromide and manganese bromide are preferable.

The concentration of the metals in the catalyst for liquid phase oxidation to raw material for oxidation is in the range of 0.1 to 1% by weight and preferably 0.2 to 0.7% by weight as metal atom. Regarding the percentage of each metal content to total amount of the metals, it is preferable that cobalt content is 40 to 65% by weight; manganese content is 30 to 55% by weight and zirconium content is 1 to 5% by weight to total amount of the metals in the catalyst.

The concentration of bromine in the catalyst for liquid phase oxidation to raw material for oxidation is in the range of 0.08 to 0.8% by weight and preferably 0.1 to 0.5% by weight. The atomic ratio of bromine to metals in the catalyst is in the range of 0.1 to 2 and preferably in the range of 0.2 to 1.5.

It is preferable that the liquid phase oxidation is performed at at least two stages by changing the catalyst concentration and the reaction temperature.

As a method for adding the catalyst, the metals and the bromine can be added by dividing respectively. That is, for example, the reaction is started by initial addition of both the metals and the bromine at the first stage and then the remainder of the metals and/or the bromine can be added step by step or continuously. The preferred embodiment includes a method comprising performing addition of bromine, at least two stages wherein bromine of above 0 and 55% by weight or below to total amount of bromine is added at the first stage and the remainder of bromine is added at the final stage.

The reaction temperature is, at the first stage, in the range of 120 to 170° C. and preferably in the range of 130 to 160° C. and at the final stage, in the range of 190 to 240° C. and preferably in the range of 200 to 230° C. The reaction pressure is, at the first stage, in the range of 0.3 to 0.8 MPa and preferably in the range of 0.4 to 0.7 MPa and at the final stage, in the range of 1.5 to 3 MPa and preferably in the range of 1.6 to 2.9 MPa.

In the oxidation reaction, an oxygen-containing gas is used. Examples of the oxygen-containing gas include oxygen gases and a mixed gas of oxygen and an inert gas such as nitrogen and argon. Among them, air is most usually applied.

As the oxidation reactor, a stirring vessel or a bubble tower is used. Among them, a stirring vessel is preferable since stirring inside the reactor can be sufficiently performed. The reactor type may be a batch type or a continuous type. Among them, a batch type is preferable.

The oxygen concentration in an exhaust gas from the reactor is 0.1 to 8% by volume and preferably 1 to 5% by volume.

The reactor is equipped with a reflux condenser to condense a large amount of solvent entrained with exhaust gas and water produced in the oxidation reaction. Condensed solvent and water are usually refluxed to the reactor and a portion thereof is also withdrawn outside the reaction system in order to adjust the water concentration inside the reactor. The reaction time is usually 30 to 100 minutes.

The oxidation reaction mixture is cooled to the range of 10 to 120° C. and preferably to the range of 20 to 40° C. to filter out deposited crystal. Then, trimellitic acid thus obtained is heat dehydrated at 210 to 240° C. and then subjected to vacuum distillation without particular purification, whereby trimellitic anhydride which is not colored can be obtained.

In the present invention, trimellitic acid and/or trimellitic anhydride obtained in above-mentioned process is further subjected to heat treatment in the presence of a catalyst comprising Ni, whereby organic bromine compounds as by-products are decomposed and changed to high boiling substances so as to able to be separated by distillation. That is, the above-mentioned heat treatment in the present invention may be performed in the dehydration step comprising heat dehydration of trimellitic acid or after the completion of dehydration of trimellitic acid. Decomposition of the organic bromine compounds contained in crude trimellitic anhydride and its change to high boiling substances little occur by mere heat treatment in which the catalyst comprising Ni is not added.

The amount of Ni in the catalyst for heat treatment is 10 ppm or above and preferably 100 ppm or above as Ni concentration to trimellitic acid and/or crude trimellitic anhydride.

The temperature of heat treatment is 200° C. or above. The higher the temperature, the shorter is the time of heat treatment, but above 300° C. decomposition of trimellitic anhydride is not negligible. The time of heat treatment necessitates 30 minutes or above and is selected depending on the temperature of heat treatment.

The organic bromine compounds difficult to separate by distillation are decomposed and changed to high boiling substances by such heat treatment, whereby they can be removed by distillation.

Although a vessel to be exclusively used for heat treatment may be equipped, the heat treatment can be performed also in a dehydrator for trimellitic acid or in a bottom section of a distillation column for separation of trimellitic anhydride. Particularly, in a bottom section of a distillation column, effective decomposition and change to high boiling substances can be performed since Ni is concentrated and residence time is long.

In the heat treatment, decomposition of organic bromine compounds or its change to high boiling substances can be further promoted by adding simultaneously at least one element selected from the group consisting of Cr, Mn, Fe, Co, Cu and Pd as a promoter of Ni catalyst. The element(s) is (are) added in the form of a metal(s) of the element(s) or a salt(s) thereof in an amount of 5 ppm or above and effectively 20 ppm or above as a concentration of a metal(s) of the element(s) to trimellitic acid and/or crude trimellitic anhydride to perform heat treatment, whereby decomposition of organic bromine compounds or its change to high boiling substances are further promoted.

In the present invention, after the completion of the heat treatment to decompose or change organic bromine compounds to high boiling substances or while performing the heat treatment, trimellitic anhydride is obtained by distillation. The distillation is performed under the condition of a reduced pressure of 50 torr or below. Regarding a method of the distillation, simple distillation is satisfactory. In order to enhance further distillation efficiency, rectification also may be applied. Regarding processes for dehydration, heat treatment and distillation, all of a batch process, semi-batch process and a continuous process may applied. Among them, a continuous process is most preferable.

In the present invention, trimellitic acid produced by the process for production of the present invention is subjected to heat treatment in the presence of a catalyst comprising 10 ppm or above of Ni at a temperature of 200° C. or above for 30 minutes or above, whereby trimellitic anhydride in which obtained trimellitic anhydride is not colored and contents of by-products such as organic bromine compounds are very small can be produced. On the other hand, trimellitic acid produced by liquid phase oxidation of psuedocumene containing below 5% by weight of dimethyl benzaldehyde and/or oxide derivative of dimethyl benzaldehyde in the presence of a catalyst comprising a bromine compound is subjected to heat treatment at a temperature of 200° C. or above for 30 minutes or above, whereby trimellitic anhydride in which trimellitic anhydride is not comparatively colored and contents of by-products such as organic bromine compounds are very small can be produced. However, in order to obtain trimellitic anhydride which is not colored to a remarkable degree, it is very preferable to contain 5% by weight or above of dimethyl benzaldehyde in psuedocumene in the production of trimellitic acid by liquid phase oxidation of psuedocumene.

PREFERRED EMBODIMENT OF THE INVENTION

The present invention will be described in more detail below, referring to Examples, which are not intended to limit the scope of the present invention.

The properties in Examples and Comparative Examples were measured according to the following methods.

[Melt Color]

50 g of trimellitic anhydride was taken in a test tube and then subjected to heat treatment at 190° C. for one hour, The color of trimellitic anhydride thus heat treated was visually compared with APHA standard color prepared according to the method described in 6.2 of JIS K1557.

[Br Compound and Bromine content]

The measurement was preformed by a fluorescent X ray. In Table 1,

PQ: psuedocumene

DBAL: 2,4-dimethyl benzaldehyde

TM: trimellitic acid.

The word "Br compound (ppm)" in Table 1 means a Br concentration (ppm) as sum total of inorganic Br compound and organic Br compound in trimellitic acid obtained by liquid phase oxidation.

The word "melt color of product" means melt color (APHA) of trimellitic anhydride.

EXAMPLE 1

A titanium autoclave of capacity 2 L, equipped with a gas exhaust tube having a reflux condenser, a gas injection tube and a stirrer was used as a reactor. 168 g of psuedocumene and 20 g of 2,4-dimethyl benzaldehyde as the raw material and 375 g of aqueous 5 wt % acetic acid as the solvent were charged to the reactor. Cobalt acetate tetrahydrate, manganese acetate tetrahydrate zirconium acetate and hydrogen bromide as the catalyst were added thereto so as to form cobalt concentration 2300 ppm, manganese concentration 2000 ppm, zirconium concentration 60 ppm and bromine concentration 140 ppm to the raw material (pusedocumene and 2,4-dimethyl aldehyde). The interior of the reactor was heated under a nitrogen atmosphere and the reaction was performed for 20 minutes at 165° C. under a pressure of 0.5 MPa while introducing air thereto, followed by further adding thereto manganese acetate tetrahydrate, zirconium acetate and hydrogen bromide as the catalyst so as to form manganese concentration 200 ppm, zirconium concentration 40 ppm and bromine concentration 2660 ppm to the raw material and continuing the reaction under a pressure of 2 MPa at 220° C. for 45 minutes.

At this time, total concentration of the metals to the raw material was 4600 ppm and total concentration of bromine to the raw material was 2800 ppm.

After the completion of the reaction, the reaction mixture was cooled to 50° C. and then the slurry thus obtained was filtered and rinsed with aqueous 95 wt % acetic acid, whereby a crystal of crude trimellitic acid was obtained. Further, the crude trimellitic acid was dehydrated at 230° C. for one hour under a nitrogen atmosphere. Trimellitic anhydride thus obtained was vacuum distilled under 15 torr in a distillation column corresponding to 10 plates as theoretical plate number.

The yield of trimellitic acid to the raw material was 86.8 mol % and combustion percentage was 6.8 mol %. The content of Br compound in trimellitic acid was 220 ppm. The melt color (APHA) of trimellitic anhydride was 60. The results were shown in Table 1.

EXAMPLE 2

The experiment was performed in the same manner as in Example 1 except that the raw material was changed to 150 g of psuedocumene and 42 g of 2,4-dimethyl benzaldehyde. The results were shown in Table 1.

EXAMPLE 3

The experiment was performed in the same manner as in Example 1 except that the raw material was changed to 96 g of psuedocumene and 105 g of 2,4-dimethyl benzaldehyde. The results were shown in Table 1.

EXAMPLE 4

The experiment was performed in the same manner as in Example 1 except that the raw material was changed to 176 g of psuedocumene and 11 g of 2,4-dimethyl benzaldehyde. The results were shown in Table 1.

COMPARATIVE EXAMPLE 1

The experiment was performed in the same manner as in Example 1 except that the raw material was changed to 191 g of psuedocumene and 0 g of 2,4-dimethyl benzaldehyde. The results were shown in Table 1.

COMPARATIVE EXAMPLE 2

191 g of psuedocumene as the raw material and 375 g of aqueous 5 wt % acetic acid as the solvent were charged to the same reactor as in Example 1. Cobalt acetate tetrahydrate, manganese acetate tetrahydrate, zirconium acetate and hydrogen bromide as the catalyst were added thereto so as to form cobalt concentration 2200 ppm, manganese concentration 1000 ppm, zirconium concentration 40 ppm and bromine concentration 600 ppm to the raw material (psuedocumene). The interior of the reactor was heated under a nitrogen atmosphere and the reaction was performed for 20 minutes at 165° C. under a pressure of 0.5 MPa while introducing air thereto, followed by further adding thereto cerium acetate monohydrate, zirconium acetate and hydrogen bromide as the catalyst so as to form cerium concentration 1000 ppm, zirconium concentration 20 ppm and bromine concentration 2600 ppm to the raw material and continuing the reaction under a pressure of 2 MPa at 220° C. for 45 minutes.

At this time, total concentration of the metals to the raw material was 4260 ppm and total concentration of bromine to the raw material was 3200 ppm.

After the completion of the reaction, the reaction mixture was cooled to 50° C. and then the slurry thus obtained was filtered and rinsed with aqueous 95 wt % acetic acid, whereby a crystal of crude trimellitic acid was obtained. Further, the crude trimellitic acid was dehydrated at 230° C. for one hour under a nitrogen atmosphere. Trimellitic anhydride thus obtained was vacuum distilled under 15 torr in a distillation column corresponding to 10 plates as theoretical plate number. The results were shown in Table 1.

COMPARATIVE EXAMPLE 3

191 g of psuedocumene as the raw material and 375 g of aqueous 5 wt % acetic acid as the solvent was charged to the same reactor as in Example 1. Cobalt acetate tetrahydrate, manganese acetate tetrahydrate, titanium tetrachloride, and hydrogen bromide as the catalyst were added thereto so as to form cobalt concentration 1700 ppm, manganese concentration 1000 ppm, titanium concentration 70 ppm and bromine concentration 460 ppm to the raw material (psuedocumene). The interior of the reactor was heated under a nitrogen atmosphere and the reaction was performed for 20 minutes at 165° C. under a pressure of 0.5 MPa while introducing air thereto, followed by further adding thereto cerium acetate monohydrate, titanium tetrachloride and hydrogen bromide as the catalyst so as to form cerium concentration 640 ppm, titanium concentration 70 ppm and bromine concentration 1460 ppm to the raw material and continuing the reaction under a pressure of 2 MPa at 220° C. for 45 minutes.

At this time, total concentration of the metals to the raw material was 3480 ppm and total concentration of bromine to the raw material was 1920 ppm.

After the completion of the reaction, the reaction mixture was cooled to 50° C. and then the slurry thus obtained was filtered and rinsed with aqueous 95 wt % acetic acid, whereby a crystal of crude trimellitic acid was obtained. Further, the crude trimellitic acid was dehydrated at 230° C. for one hour under a nitrogen atmosphere. Trimellitic anhydride thus obtained was vacuum distilled under 15 torr in a distillation column corresponding to 10 plates as theoretical plate number. The results were shown in Table 1.

EXAMPLE 5

The experiment was performed in the same manner as in Example 1 except that the raw material was changed to 150 g of psuedocumene, 21 g of 2,4-dimethyl benzaldehyde and 21 g of 2,4-dimethyl benzoic acid. The yield of trimellitic acid to the raw material was 88.0 mol % and combustion percentage 5.0 mol %. The content of Br compound in trimellitic acid was 35 ppm. The melt color (APHA) of trimellitic anhydride was 45.

As clear from Examples 1 to 5, the yield of trimellitic acid is more improved and Br content is more decreased by performing liquid phase oxidation of psuedocumene containing dimethyl benzaldehyde as the raw material than in conventional processes. Further, a high purity of trimellitic anhydride which is not colored can be obtained from trimellitic acid thus obtained.

EXAMPLE 6

500 g of water, 7 g of hydrogen bromide and 7.5 g of manganese bromide tetrahydrate as the catalyst liquid were charged to a reactor formed of a zirconium autoclave of inner capacity 2 L, equipped with a reflux condenser, a stirrer, a heater, a raw material feeding port, a gas introducing port and a reaction product withdrawing port. A pressure was applied to the interior of the reactor with nitrogen and the temperature of the interior was elevated. After the temperature reached to 230° C. , 2,4-dimethyl benzaldehyde with purity 99% or above at the rate of 125 g/hr and the catalyst liquid with the same component as in above-mentioned catalyst liquid at the rate of 500 g/hr each separately, were fed to the reactor. Introduction of air was started simultaneously with feeding of 2,4-dimethyl benzaldehyde and a flow rate of air was controlled so as to maintain oxygen in an exhaust gas from the reactor to 3 to 4%. The reaction products were withdrawn at the rate of about 700 g/hr while maintaining the liquid level in the reactor to a constant liquid level.

The reaction products which formed a slurry in the cooled state were filtered to perform solid-liquid separation, thus obtaining 185 g/hr of crude trimellitic acid.

Crude trimellitic acid thus obtained was continuously fed to a dehydrator at the rate of 165 parts by weight per one hour and heat dehydrated under atmospheric pressure at 230° C. in a residence time of 3 hours and then the dehydration-treated liquid was withdrawn so as to maintain the liquid level in the dehydrator to a constant liquid level. The dehydration percentage of trimellitic acid in the dehydrator was 90%. Nickel acetate tetrahydrate was added to the dehydration-treated liquid so as to form Ni concentration 100 ppm to the dehydration-treated liquid. The liquid thus obtained was continuously fed to a distillation column with a reduced pressure degree of 15 torr and a theoretical plate number of 2 plates. The amount to be withdrawn from a bottom section of the distillation column was 3 parts by weight per one hour. Average residence time at the column bottom section was 55 hours and the temperature of the column bottom section was 256° C. Ni was concentrated in the column bottom section as a high boiling matter. Trimellitic anhydride thus distilled had purity 98.7% and bromine content 100 ppm.

COMPARATIVE EXAMPLE 4

The experiment was performed in the same manner as in Example 6 except that nickel acetate tetrahydrate was not added to the dehydration-treated liquid. The amount to be withdrawn from the column bottom section was 3 parts by weight per one hour. Average residence time at the column bottom section was 55 hours and the temperature of the column bottom section was 255° C. Trimellitic anhydride thus distilled had purity 98.7% and bromine content 200 ppm.

EXAMPLE 7

The experiment was performed in the same manner as in Example 6 except nickel acetate tetrahydrate and iron oxalate dihydrate were added to the dehydration-treated liquid so as to form Ni concentration 100 ppm and Fe concentration 25 ppm to the dehydration-treated liquid. Average residence time at the column bottom section was 55 hours and the temperature of the column bottom section was 256° C. Ni and Fe were concentrated in the column bottom section as high boiling matters. Trimellitic anhydride thus distilled had purity 98.7% and bromine content 50 ppm.

COMPARATIVE EXAMPLE 5

The experiment was performed in the same manner as in Example 6 except that iron oxalate dihydrate instead of nickel acetate tetrahydrate was added to the dehydration-treated liquid so as to form Fe concentration 100 ppm to the dehydration-treated liquid. Trimellitic anhydride thus distilled had purity 98.7% and bromine content 200 ppm.

As clear from Examples 6 and 7, crude trimellitic acid is heat treated in the presence of Ni and distilled according to the process of the present invention, whereby a bromine content in trimellitic anhydride thus obtained can be reduced.

According to the present invention, a high quality of trimellitic anhydride can be produced with industrial advantages, whereby high grade plasticizers and heat resisting plastics can be obtained. Thus, the present invention has a large industrial significance.

TABLE 1

| Item | Example 1 | Example 2 | Example 3 | Example 4 | Comp. Ex. 1 | Comp. Ex. 2 | Comp. Ex. 3 |
|---|---|---|---|---|---|---|---|
| PQ (mol %) | 90 | 80 | 50 | 95 | 100 | 100 | 100 |
| DBAL (mol %) | 10 | 20 | 50 | 5 | 0 | 0 | 0 |
| Yield of TM (mol %) | 86.8 | 87.7 | 88.8 | 86.3 | 84.5 | 86.6 | 84.7 |
| Combustion percentage (mol %) | 6.8 | 6.9 | 5.1 | 7.2 | 9.1 | 7.0 | 10.0 |
| Br compound (ppm) | 220 | 140 | 90 | 220 | 280 | 280 | 160 |
| Melt color of product (APHA) | 60 | 50 | 50 | 70 | 110 | 90 | 120 |

Note:
PQ; psuedocumen
DBAL; 2,4-dimethyl benzaldehyde
TM; trimellitic acid

What is claimed is:

1. A process for producing trimellitic anhydride which comprises performing liquid phase oxidation of a raw material comprising pseudocumene containing 5% by weight or above of a dimethyl benzaldehyde with air in an aliphatic monocarboxylic acid having 1 to 5 carbon atoms as a solvent in the presence of a catalyst comprising both each metal of cobalt, manganese and zirconium and bromine to obtain trimellitic acid and then heat dehydrating trimellitic acid thus obtained, thereby producing trimellitic anhydride.

2. The process according to claim 1, wherein the metals and the bromine in said catalyst are added in at least two stages.

3. The process according to claim 1, dividing addition of bromine in said catalyst into at least two stages wherein above 0% and less than or equal to 55% by weight of the total amount of bromine is added at the first stage and the remainder of bromine is added at the final stage and a temperature at the first stage is 120 to 170° C. and a temperature at the final stage is 190 to 240° C.

4. The process according to claim 1, wherein total amount of metals of cobalt, manganese and zirconium in said catalyst is 0.1 to 1% by weight as metal atom to amount of the raw material for oxidation.

5. The process according to claim 1, wherein cobalt content is 40 to 65% by weight and manganese content is 30 to 55% by weight and zirconium content is 1 to 5% by weight to total amount of metals in said catalyst.

6. The process according to claim 1, wherein an amount of the bromine in said catalyst is used 0.08 to 0.8% by weight as bromine atom to the raw material for oxidation.

7. The process according to claim 1, wherein a weight ratio of the solvent to the raw material for oxidation is 1/1 to 4/1.

8. The process according to claim 1, performing heat dehydration at a temperature of 210 to 240° C.

9. A process for producing trimellitic anhydride which comprises heat dehydrating trimellitic acid produced in claim 1 to produce trimellitic anhydride and then separating trimellitic anhydride thus produced by vacuum distillation.

10. A process for producing trimellitic anhydride which comprises performing liquid phase oxidation of pseudocumene containing 5% by weight or above of dimethyl benzaldehyde with air in aliphatic monocarboxylic acid having 1 to 5 carbon atoms as a solvent in the presence of a catalyst comprising both each metal of cobalt, manganese and zirconium and bromine to obtain a reaction product comprising trimellitic acid; and then heat treating the reaction product comprising trimellitic acid thus obtained in the presence of a catalyst comprising Ni, with the ratio of Ni to trimellitic acid being 10 ppm or above, at a temperature of 200° C. or above for 30 minutes or above to produce trimellitic anhydride; and then separating trimellitic anhydride thus produced by distillation.

11. The process according to claim 10, wherein at least one element selected from the group consisting of Cr, Mn, Fe, Co, Cu and Pd is further contained in said catalyst as promoter of Ni and the ratio of said element to trimellitic acid is 5 ppm or above.

12. The process according to claim 10, performing heat treatment in a bottom section of a distillation column.

13. A process for producing trimellitic anhydride which comprises heat treating trimellitic acid produced in claim 1 in the presence of a catalyst comprising 10 ppm or above of Ni to trimellitic anhydride at a temperature of 200° C. or above for 30 minutes or above and then separating trimellitic anhydride by distillation.

14. A process for producing trimellitic anhydride which comprises heat treating a mixture of;

(a) trimellitic acid obtained by performing liquid phase oxidation of a raw material comprising pseudocumene containing 5% by weight or above of a dimethyl benzaldehyde with air in an aliphatic moncarboxylic acid having 1 to 5 carbon atoms as a solvent in the presence of a catalyst comprising both each metal of cobalt, manganese and zirconium and bromine and (b) trimellitic anhydride obtained by performing liquid phase oxidation of a raw material comprising pseudocumene containing 5% by weight or above of a dimethyl benzaldehyde with air in an aliphatic monocarboxylic acid having 1 to 5 carbon atoms as a solvent in the presence of a catalyst comprising both each metal of cobalt, manganese and zirconium and bromine to obtain trimellitic acid and then heat dehydrating trimellitic acid thus obtained, in the presence of a catalyst comprising 10 ppm or above of Ni to the mixture and at temperature of 200° C. or above for 30 minutes or above and then separating trimellitic anhydride thus produced by distillation.

15. A process for producing trimellitic anhydride which comprises performing liquid phase oxidation of pseudocumene, dimethyl benzaldehyde and/or oxide derivative of dimethyl benzaldehyde as raw material for oxidation with air in a solvent in the presence of a catalyst comprising a bromine compound to obtain trimellitic acid and then heat treating trimellitic acid thus obtained in the presence of a catalyst comprising 10 ppm or above of Ni to trimellitic acid and/or trimellitic anhydride at a temperature of 200° C. or above for 30 minutes or above to produce trimellitic anhydride and then separating trimellitic anhydride thus produced by distillation.

16. The process according to claim 15, wherein at least one element selected form the group consisting of Cr, Mn, Fe, Co, Cu and Pd is further contained in said catalyst as promoter of Ni and the ratio of said element to trimellitic acid is 5 ppm or above.

17. The process according to claim 15, performing heat treatment in a bottom section of a distillation column.

* * * * *